United States Patent [19]

Weiss et al.

[11] Patent Number: 5,981,165
[45] Date of Patent: Nov. 9, 1999

[54] IN VITRO INDUCTION OF DOPAMINERGIC CELLS

[75] Inventors: Samuel Weiss; Brent Reynolds, both of Alberta, Canada

[73] Assignee: NeuroSpheres Holdings Ltd., Calgary, Canada

[21] Appl. No.: 08/482,079

[22] Filed: Jun. 7, 1995

Related U.S. Application Data

[63] Continuation-in-part of application No. 08/339,090, Nov. 14, 1994, abandoned, which is a continuation-in-part of application No. 08/270,412, Jul. 5, 1994, abandoned, which is a continuation of application No. 07/726,812, Jul. 8, 1991, abandoned.

[51] Int. Cl.$^6$ .............................. C12Q 1/00; C12N 5/00; A61K 38/30

[52] U.S. Cl. ........................... 435/4; 424/93.7; 435/325; 514/2; 530/399

[58] Field of Search ............................... 424/92 R, 93.7; 435/1, 240.2, 4, 325; 514/2; 530/399

[56] References Cited

U.S. PATENT DOCUMENTS

| | | | |
|---|---|---|---|
| 5,082,670 | 1/1992 | Gage et al. | 424/520 |
| 5,411,883 | 5/1995 | Boss et al. | 435/29 |

FOREIGN PATENT DOCUMENTS

| | | |
|---|---|---|
| 0 412 554 B1 | 2/1999 | European Pat. Off. . |
| WO 93/06116 | 4/1993 | WIPO . |
| WO 94/03199 | 2/1994 | WIPO . |

OTHER PUBLICATIONS

Engele and Bohn. J. Neurosci., vol. 11(10):3070–3078, Oct. 1, 1991.
Cattaneo and McKay. Nature vol. 347:762–765, Oct. 25, 1990.
Beyer et al, *Neurosci. Lett.*, 128: 1–3, (1991) "Cells from embryonic rat striatum cocultured with mesencephalic glia express dopaminergic phenotypes".
Casper et al., *J. Neurosci. Res.*, 30: 372–381 (1991) "EGF Enhances the survival of dopamine neurons in rat embryonic mesencephalon primary cell culture".
Dal Toso et al. *J. Neurosci.*, 8(3): 733–745 (1988) "Development and survival of neurons in dissociated fetal mesencephalic serum–free cell cultures: I. effects of cell density and of an adult mammalian striatal–derived neuronotrphilic factor (SDNF)".
Denis–Donini, *Nature,* 339: 701–703, (1989) "Expression of dopaminergic phenotypes in the mouse olfactory bulb induced by the calcitonin gene–related peptide".
Engele, J., et al., *J. Neurosci. Res.*, 30: 359–371, (1991) "Conditioned media derived from glial cell lines promote survival and differentiation of dopaminergic neurons in vitro: role of mesencephalic glia".
Ferrari et al. *Dev. Biol.,* 133: 140–147 (1989) "Basic fibroblast growth factor promotes the survival and development of mesencephalic neurons in culture".

Gaul and Lübbert, *Proc. R. Soc. Lond. B,* 249: 57–63, (1992) "Cortical astrocytes activated by basic fibroblast growth factor secrete molecules that stimulate differentiation of mesencephalic dopaminergic neurons".
Hama et al., *Neurosci.,* 40(2): 445–452 (1991) "Interleukin–6 improves the survival of mesencephalic catecholaminergic and septal cholinergic neurons from postnatal, two–week–old rats in cultures".
Hartikka et al., *J. Neurosci. Res.*, 32: 190–201, (1992) "Cyclic AMP, but not basic FGF, increases the in vitro survival of mesencephalic dopaminergic neurons and protects them from $MPP^+$–induced degeneration".
Hyman et al., *Nature,* 350: 230–232, (1991) "BDNF is a neurotrophic factor for dopaminergic neurons of the substantia nigra".
Lehndahl et al., *Cell,* 60: 585–595 (1990) "CNS stem cells express a new class of intermediate filament protein".
Lin, L.H., et al., *Science,* 260: 1130–1132 (1993) "GDNF: a glial cell line–derived neurotrophic factor for midbrain dopaminergic neurons".
Mayer, E., *Dev. Brain Res.,* 72(2): 253–258 (1993) "Mitogenic effect of basic fibroblast growth factor on embryonic ventral mesencephalic dopaminergic neurone precursors."
Morshead and van der Kooy, *J. Neurosci.,*12(1): 249–256 (1992) "Postmitotic death is the fate of constitutively proliferating cells in the subependymal layer of the adult mouse brain".
Reynolds and Weiss, *Restorative Neurology and Neuroscience,* 4(3): 208 (1992), Abstract No. 34.P3 "A non–transformed, growth factor–dependent stem cell line derived from the embryonic mouse CNS produces neurons, astrocytes and oligodendrocytes".
Reynolds et al., *J. Neurosci.,* 12(11): 4565–4574 (1992) "A Multipotent EGF–responsive striatal embryonic progenitor cell produces neurons and astrocytes".
Reynolds and Weiss, *Science,* 255: 1707 (1992) "Generation of neurons and astrocytes from isolated cells of the adult mammalian central nervous system".
Reynolds and Weiss, *Neuronal Cell Death and Repair,* Ch. 19 ed. Cuello (1993) "EGF–responsive stem cells in the mammalian central nervous system".

(List continued on next page.)

*Primary Examiner*—Nancy Degen
*Assistant Examiner*—William Sandals
*Attorney, Agent, or Firm*—Burns, Doane, Swecker & Mathis, L.L.P.

[57] ABSTRACT

A culture method for inducing the expression of tyrosine hydroxylase in neural cells is provided. Mammalian CNS neural cells are cultured in the presence of a fibroblast growth factor and at least one selected from a member of the transforming growth factor beta family, a feeder layer bed of cells, and cell conditioned medium. Cells cultured as provided above may be transplanted to provide dopaminergic cells to a patient. The cells may also be used in methods for drug screening.

41 Claims, 2 Drawing Sheets

OTHER PUBLICATIONS

Satoh et al. *Dev. Brain Res.*, 53(1): 1–5, (1990) "Tyrosine hydroxylase–immunoreactive neurons in the mouse cerebral cortex during the postnatal period".

Schubert et al., *Nature*, 249: 224, (1974) "Clonal cell lines from the rat central nervous system".

Takeshima et al. *J. Neurosci.*, 14(8): 4769–4779, (1994) "Mesencephalic Type 1 astrocytes rescue dopaminergic neurons from death induced by serum deprivation".

Tashiro et al., *Neurosci. Lett.*, 97: 6–10, (1989) "Tyrosine hydroxylase–like immunoreactive neurons in the striatum of the rat".

Schubert, et al., *Nature*, 344 p. 868 (1990) "Activin is a nerve cell survival molecule."

Du, et al., *Journal of Neuroscience*, 14(12) p. 7688 (1994) "Novel expression of the tyrosine hydroxylase gene requires both acidic fibroblast growth factor and an activator."

Widner et al., *New England Journal of Medicine*, 327(22) p. 1556 (1992) "Bilateral fetal mesencephalic grafting in two patients with parkinsonism induced by 1–methyl–4–phenyl–1,2,3,6–tetrahydropyridine (MPTP)."

Silani et al., *Experimental Neurology*, 128 p. 59 (1994) "Development of dopaminergic neurons in the human mesencephalon and in Vitro effects of basic fibroblast growth factor treatment."

Morrison et al. Basic fibroblast growth factor supports the survival of cerebral cortical neurons in primary culture. PNAS (USA) 83:7537–7541, Oct. 1986.

Hatten et al. In vitro neurite extensino by granule neurons is dependent upon astroglial–derived fibroblast growth factor. Dev. Biol. 125:280–289, 1988.

Lo et al. V–myc immortalization of early rat neurla crest cells yields a clonal cell line which generates both glial and adrenergic progenitor cells. Dev. Biol. 145:139–153, May 15, 1991.

Schubert and Kimura. Substratum–growth factor collaborations are required for the mitogenic activities of activin and FGF on embryonal carcinomal cells. J. Cell Biol. 114(4):841–846, Aug. 1991.

Henderson et al.. Neurotrophic factors in development and plasticity of spinal neurons. Res. Neurobiol. Neurosci. 5:15–28, 1993.

Lefebvre et al. Growth factor inteactions in cultures of dissociated adult acoustic ganglia: Neuronotrophic effects. Brain Res. 567:306–312, 1991.

Lillein et al. Control of proliferation in the retina: temporal changes in responsiveness to FGF and TGFalpha. Development 115:253–266, 1992.

Lindvall et al. Grafts of fetal dopamine neurons survive and improve motor function in Parkinson's disease. Science vol. 247:574–577, Feb. 2, 1990.

Freed et al. Transplantation of human fetal dopamine cells for Parkinson's disease. Arch. Neurol. vol. 47:505–512, May 1990.

Zhou, et al. *Developmental Brain Res. 81*, pp. 318–324 (1994) "The Stimulatory Effect of brain–derived neurotrophic factor on dopaminergic phenotype expression of embryonic rat cortical neurons in vitro."

Iacovitti, et al. *Molecular Brain Res. 16*, pp. 215–222 (1992) "Muscle–derived differentiation factor increases expression of the tyrosine hydroxylase gene and enzyme activity in cultured dopamine neurons from the rat midbrain."

Steinbusch, et al. *Progress in Brain Res. 82* pp. 81–86 (1990) "Basic fibroblast growth factor enhances survival and sprouting of fetal dopaminergic cells implanted in the denervated rat caudate–putamen: preliminary observations."

Gaul and Lübbert, "Cortical astrocytes activated by basic fibroblast growth factor secrete molecules that stimulate differentiation of mesencephalic dopaminergic neurons," *The Royal Society, Proceedings: Biological Sciences*, 249(1324)57–63 (Jul. 1992).

Kaplan, "Formation and Turnover of Neurons in Young and Senescent Animals: An Electronmicroscopic and Morphometric Analysis," *Annals New York Academy of Sciences*, 457:173–192 (1985).

IN VITRO INDUCTION OF DOPAMINERGIC CELLS

RELATED APPLICATIONS

This application is a continuation-in-part of U.S. Ser. No. 08/339,090, filed Nov. 14, 1994 now abandoned, which is a continuation-in-part of U.S. Ser. No. 08/270,412 filed Jul. 5, 1994 now abandoned which is a continuation application of U.S. Ser. No. 07/726,812 filed Jul. 8, 1991 now abandoned.

BACKGROUND OF THE INVENTION

It has been established that the phenotypic expression and survival of differentiating neural cells and the survival and metabolism of established neural cells is directed by a variety of extracellular signals. Neighboring cells and processes surrounding neural cells, play an important role in the regulation of cell differentiation, metabolic function and survival, largely through their release of growth and other regulatory factors.

Many neurological disorders, including Parkinson's disease, are the result of the degeneration of specific groups of neural cells. In the case of Parkinson's disease, the degeneration of a group of dopamine-containing cells, which connect the ventral tegmentum and substantia nigra (located in the ventral portion of the mesencephalon, or midbrain) with the striatum, have been implicated in the etiology of the condition.

In order to understand the factors which result in, or could prevent, the degeneration of these dopaminergic pathways, tissue obtained from the mesencephalon region has been extensively studied. Embryonic dopamine-containing neurons, derived from mesencephalic tissue, are difficult to culture as the dopaminergic neurons do not survive well in culture. However, these cultures show an enhanced survival and/or a modified biochemical activity when cultured with a conditioned medium or when treated with growth factors. Embryonic tissue from the mesencephalon has been grown in conditioned culture media (CM) derived from the rat B49 glial cell line, the R 33 neural retina glial cell line and the J S Schwannoma cell line [Engele, J., et al., *J. Neurosci. Res.*, 30: 359–371, (1991)]. In all three cases, CM significantly increased the survival of the cultured dopaminergic neurons. The enhanced survival of the dopaminergic neurons was not due to the proliferation of dopaminergic cells but was attributed to the effects of the CM on existing glial cells derived from the mesencephalic culture and the resultant interactions between the glial cells and the dopaminergic neurons, rather than to a direct effect on the dopaminergic neurons.

Culturing embryonic mesencephalic tissue in CM prepared from mesencephalic astrocytes, or co-culturing the tissue on a layer of mesencephalon-derived astrocytes, rescues dopaminergic neurons from death induced by serum deprivation. Astrocytes or the CM prepared from astrocytes from the striatum and cerebral cortex had significantly weaker protective effects [Takeshima et al. *J. Neurosci.*, 14(8): 4769–4779, (1994)]. In one report, CM derived from cortical astrocytes had no effect on dopaminergic cell survival or proliferation but did alter the biochemistry of this population of cells, resulting in a small increase in their uptake of dopamine [Gaul and Lübbert, *Proc. R. Soc. Lond.* B, 249: 57–63, (1992)].

Growth factors, many of which are present in CM from neural tissue, are believed to be responsible for regulating dopaminergic neuron survival and metabolism, either directly, or through their effects on adjacent cells. Growth factors reported to have a direct effect on dopaminergic neuron survival include interleukin-6 (IL-6) [Hama et al., *Neurosci.*, 40(2): 445–452 (1991)], brain-derived neurotrophic factor (BDNF) [Hyman et al., *Nature*, 350: 230–232, (1991)], basic fibroblast growth factor (FGF-2, formally referred to as bFGF) [Dal Toso et al. *J. Neurosci.*, 8(3): 733–745 (1988); Ferrari et al. *Dev. Biol.* 133: 140–147 (1989); and glial cell line-derived neurotrophic factor (GDNF), secreted by the rat B49 cell line [Lin, L. G., et al, *Science*, 260: 1130–1132 (1993)], all of which specifically enhance the survival of dopaminergic neurons in dissociated rat or mouse embryo mesencephalon cultures without increasing neuron or glial cell numbers. GDNF dramatically increases the morphological differentiation of dopaminergic neurons, resulting in more extensive neurite outgrowth and increased cell body size. Some growth factors, such as nerve growth factor (NGF) (Hatanaka and Tsuki (1986), *Dev. Brains Res.* 30: 47–56), platelet-derived growth factor (PDGF) and interleukin-1 (IL-1) (Engele & Bohn (1991), *Neurosci.* 11(10): 3070–3078); Mayer, E. (1993) *Dev. Brain Res.* 72: 253–258) and nerve growth factor (NGF) (Engele & Bohn, ibid) are reported to support dopaminergic cell survival in embryonic mesencephalic tissue through a glial cell-mediated mechanism.

In vivo studies indicate that the damage caused by mechanical or chemical lesions in the dopaminergic pathways between the mesencephalon and the striatum can be significantly reduced by treatment with epidermal growth factor (EGF) [Pezzoli et al, *Movement Disorders* 6(4) 281–287, (1991)] and BDNF (Hyman et al., supra). In vitro treatment with cyclic AMP, but not FGF-2 or NGF, increased the survival of cultured mesencephalic dopaminergic neurons in response to chemically induced degeneration produced by 1-methyl-4-phenylpyridinium ($MPP^+$) [Hyman et al., supra; Hartikka et al., *J. Neurosci. Res.*, 32: 190–201, (1992)]. Although the use of a FGF-2-stimulated astrocyte CM enhances dopamine uptake, the use of this CM did not have a protective effect when the neurons were chemically lesioned using $MPP^+$ (Gaul and Lübbert, supra).

Many of the cells obtained from embryonic tissue which normally gives rise to dopaminergic neurons (i.e. normally dopaminergic tissue), such as the mesencephalon and olfactory bulb, will eventually differentiate into dopaminergic neurons under primary culture conditions. However, an increased number of cells, in tissue obtained from normally dopaminergic areas of the brain, can be induced to differentiate into dopaminergic cells by co-culturing with feeder cell layers derived from neural tissue. The dopaminergic neurons of the olfactory bulb show a five-fold increase in number when embryonic olfactory bulb neurons are co-cultured with olfactory epithelial neurons. It is believed that a soluble factor, calcitonin gene-related peptide (CGRP), which is present in the epithelial cells, is responsible for the induction of additional dopaminergic neurons in the olfactory bulb [Denis-Donini, *Nature*, 339: 701–703, (1989)]. Co-culturing rat embryonic neostriatal and substantia nigral tissue for one to three weeks on glial cell feeder layers obtained from the substantia nigra region induces the expression of dopaminergic cells as indicated by tyrosine hydroxylase immunoreactivity (TH+) in the tissue cultured from both areas. However, when the same tissues were co-cultured with glial cells from the neostriatum, dopaminergic cells were observed only in the substantia nigra tissue but not in the neostriatal tissue [Beyer et al., *Neurosci. Lett.*, 128: 1–3, (1991)]. The mechanism underlying the appearance of TH-IR in neostriatal tissue (an area which does not contain dopaminergic cells in the adult) was not determined.

However, it could have been due to the induction of TH+ cells in the substantia nigral cell feeder layer in response to the presence of the striatal tissue; to the induction of dopaminergic properties in the striatal cells; or to promotion of the survival of dopaminergic cells in striatal tissue, such cells having been reported to occur transiently during development in the striatum (Tashiro et al. (1989), *Neurosci. Lett.* 97: 6–10) and cortex (Satoh and Suzuki (1990), *Dev. Brain Res.* 53: 1–5). Small numbers of TH+ cells (140 TH+ cells/cm$^2$) have been induced in tissue from embryonic rat cortex using a combination of BDNF and dopamine, in a culture medium which contained 10% fetal calf serum. Fewer TH+ cells were seen when BDNF, or dopamine were used alone (Zhou et al. (1994), *Dev. Brain Res.* 81: 318–324). A few cells from embryonic mouse striatal tissue can be induced to express TH+ when incubated with FGF-1 and an enhanced result can be obtained using a combination of FGF-1 and an unidentified >10 kD fraction obtained from muscle tissue (Du et al. (1994) *J. Neurosci.* 14(12): 7688–7694).

The degeneration of the substantia nigra dopaminergic neurons which characterizes Parkinson's Disease is normally treated using pharmacological interventions to augment the declining natural dopamine supply to the striatum. However, there are problems associated with drug treatment such as the development of tolerance to the medication and possible side effects. Neuronal grafts, using embryonic substantia nigral tissue have shown some potential for relieving experimentally induced Parkinsonism in rodents and primates and in some human Parkinsonian patients. However, graft survival is poor and only limited quantities of embryonic dopaminergic tissue are available. On average, 4–10 fresh, human embryos are required to obtain sufficient numbers of dopaminergic neurons for a single human transplant (Widner et al., *N Engl J Med* 327: 1556–1563 (1992)). Preferred treatment would involve prevention of, or a reduction in the amount of the degeneration which occurs. Once damage has occurred, it would be preferable to replace the lost cells by implanting new dopaminergic neurons using cells derived from neural cells which have been proliferated in culture preferably from a non-tumor cell line, or from cells that have not been intentionally immortalized in order to induce proliferation and, most preferably, would be derived from a patient's own neural tissue. Alternatively, a less invasive treatment would involve the in vivo manipulation of the patient's own population of neural cells in order to replace the function of the damaged dopaminergic neurons.

The prior art suggests that cultures of dopaminergic cells can be obtained through the use of glial feeder layers, or the application of certain growth factors or conditioned media to mesencephalic tissue and other dopaminergic tissues. These treatments can induce differentiation, increase the survival, or alter the metabolism of cells from normally dopaminergic tissue that has been cultured in vitro. However, culture methods for inducing cells from other, non-dopaminergic brain regions to differentiate into dopaminergic cells are limited. While it has been demonstrated that a feeder layer of cells from regions such as the substantia nigra and olfactory bulb (areas which normally contain a relatively high population of dopaminergic cells) can be used to induce the appearance of dopaminergic cells in certain embryonic central nervous system (CNS) tissues, there is no evidence that cells from non-dopaminergic neural tissue could be used as feeder layers in tissue culture designed to induce the appearance of dopamine in tissues, such as the striatum, which do not normally contain dopamine.

For some purposes, especially transplantation and certain drug testing procedures, it would be advantageous to use completely defined culture conditions to induce the differentiation of dopaminergic cells. It would be particularly advantageous if the cells were obtained from both dopaminergic and normally non-dopaminergic neural tissue sources, thus maximizing the number of dopaminergic cells that can be generated from a single embryo.

There exists a need in the art for a reliable method of inducing neural cells, derived from all brain regions, from tissue obtained from animals of all ages, to differentiate into dopaminergic cells in the presence or absence of a feeder layer substrate. In particular, it would be advantageous to induce the expression of dopamine in cells derived from regions which do not normally contain dopaminergic cell bodies, such as the striatum, but which require dopamine for normal functioning.

Recently, it has been demonstrated that multipotent neural stem cells, obtained from embryonic, juvenile, and adult tissue, can be proliferated in vitro to generate large numbers of neural stem cell progeny, which, under appropriate conditions, can differentiate into neurons and glia (PCT applications No. WO 93/01275, WO 94/16718, WO 94/10292, and WO 94/09119). It would be advantageous to generate dopaminergic cells from the proliferated progeny of multipotent neural stem cells, derived from any area of the CNS.

Accordingly, it is an object of this invention to provide a method for inducing large numbers of neural cells obtained from normally non-dopaminergic tissue to differentiate, in vitro, into dopaminergic cells in order to provide a reliable source of dopaminergic cells for various applications such as transplantation into patients with dopamine deficiencies and for drug screening procedures.

It is a further object of the invention to provide a method of inducing the undifferentiated, proliferated progeny of multipotent neural stem cells, derived from any area of the CNS known to contain such cells, to differentiate into dopaminergic cells, in order to provide unlimited quantities of dopaminergic cells for transplantation, drug screening and other purposes.

Additionally, it is an object of the invention to provide tissue culture methods that use completely defined culture conditions, and thus do not require the presence of a feeder layer of cells, conditioned medium, or serum, to increase the number of dopaminergic cells obtained from a single embryonic brain. Such cells would have use in specific applications such as transplantation into patients with dopamine deficiencies and for certain drug screening procedures.

These and other objects and features of the invention will be apparent to those skilled in the art from the following detailed description and the appended claims.

None of the foregoing references is believed to disclose the present invention as claimed and is not presumed to be prior art. The references are offered for the purpose of background information.

SUMMARY OF THE INVENTION

A method for inducing the expression of tyrosine hydroxylase in neural cells in vitro is disclosed. The method comprises contacting neural cells with a culture medium comprising at least one member of the fibroblast growth factor family and at least one additive selected from the group consisting of conditioned medium and molecules of the transforming growth factor beta family. The method induces neural cells obtained from normally non-dopaminergic neural tissue such as the striatum and the cortex to express tyrosine hydroxylase.

A method for treating a neurological disorder in a patient requiring dopaminergic cells is also disclosed. The method comprises contacting neural cells with a culture medium comprising at least one member of the fibroblast growth factor family and at least one member of the transforming growth factor beta family to produce differentiating or differentiated dopaminergic cells and transplanting the dopaminergic cells into the patient.

DESCRIPTION OF THE DRAWINGS

FIG. 1. Dividing subependymal cells, in the subventricular zone of adult mice were labeled with repeated injections of BrdU over a 24 hour period. Within 30 minutes of the last injection, the mice were sacrificed and their brains removed. The subventricular zones were removed and the dissociated cells were cultured on poly-L-ornithine coated coverslips using complete medium with or without conditioned medium derived from the rat B49 glial cell line and FGF-2 (20 ng/ml). Three days after plating, the cells were fixed and processed for dual-label indirect immunocytochemistry for TH (Eugene Tech, polyclonal 1:1000) and BrdU (Amersham, monoclonal, 1:100). BrdU-labelled cells (dividing subependymal cells) that were also TH-immunoreactive were seen only in the experiments in which the conditioned medium and growth factor were used. (A) A single BrdU-immunoreactive cell (arrow) that is TH-immunoreactive (B, arrow) suggesting that the adult proliferating subependymal cells can be induced to express TH in the presence of the conditioned medium and growth factor.

FIG. 2. Single, undissociated six day old primary generated neurospheres were plated onto poly-L-ornithine coated glass coverslips in DMEM/F12 hormone mix medium with conditioned medium derived from the rat B49 glial cell line and FGF-2(20 ng/ml). Immunocytochemical analysis 24 hours later revealed the presence of TH+ cells. (A) Phase contrast micrograph of a neurosphere 24 hours post-plating. (B) The same sphere as in A, processed for TH-immunohistochemistry, reveals the presence of at least one TH+ cell, having neuronal morphology.

FIG. 3. Single, undissociated six day old second passage neurospheres were labelled with BrdU and plated onto a confluent bed of striatal-derived astrocytes. 24 hours post-plating, the cells were processed for dual-label indirect immunocytochemistry for TH (Eugene Tech, polyclonal 1:1000) and BrdU (Amersham, monoclonal, 1:100). (A) A BrdU-immunoreactive cell (arrow) is (B) TH-immunoreactive (arrow). (C) TH-immunoreactive cells (arrows) are also MAP-2 immunoreactive (D), demonstrating other neuronal characteristics, in addition to morphology.

DETAILED DESCRIPTION OF THE INVENTION

In Vitro Induction of Dopaminergic Cells Derived from Primary Cells Obtained From Normally Non-Dopaminergic Neural Tissues The term "dopaminergic neural tissue" refers to the tissue from regions of the CNS that are known, in the mature state, to contain significant numbers of dopaminergic cell bodies. Dopaminergic cells are neural cells whose presence in neural tissue is determined by the presence of tyrosine hydroxylase (TH) or the presence of dopamine decarboxylase and/or the absence of dopamine betahydroxylase within the cells, polymerase chain reaction techniques, or antibodies directed against dopamine. Tyrosine hydroxylase is the rate-limiting enzyme in the biochemical pathway which leads to dopamine production and is commonly used in the art as a marker for dopaminergic neurons. Dopaminergic neural tissue is found in regions of the retina, olfactory bulb, hypothalamus, dorsal motor nucleus, nucleus tractus solitarious, periaqueductal gray matter, ventral tegmenum, and substantia nigra. The term "normally non-dopaminergic neural tissue", as used herein, refers to the tissue from regions of the developed CNS that are not dopaminergic neural tissue.

Using the methods disclosed herein, primary cells obtained from dissociated neural tissue are induced to express tyrosine hydroxylase. The term "primary neural cell" refers to a cell obtained from neural tissue that has not been passaged in vitro (to a secondary culture). Primary neural cell cultures are prepared by removing tissue from an animal using any sterile procedure, dissociating the tissue to generate a suspension of primary cells, and placing the cells in any medium known to support the survival of cells. The primary cells are exposed to a culture medium comprising growth factors that induce dopamine production in cells obtained from normally non-dopaminergic neural tissue. The term "growth factor" refers to a biological factor (i.e. a biologically active substance functional in CNS cells) such as a protein, peptide, amino acid, lipid, carbohydrate, nucleic acid, nucleotide, or other substance having a growth, proliferative, differentiative, or trophic effect on neural cells, either singly, or in combination with other factors. A growth factor that induces dopamine production will bind to a receptor on a cell and induce the cell to begin to express, or increase its expression of messenger RNA (mRNA) for dopamine precursor molecules and enzymes involved in dopamine production. A preferred growth factor is a member of the fibroblast growth factor family (e.g. FGF-1 or FGF-2), or equivalent growth factors that are capable of binding to FGF receptors on the cells. FGF and equivalent growth factors can be used singly or in combination with other growth factors. Growth factors are generally added at concentrations of about 1 to 100 ng/ml, usually about 5 ng/ml to 60 ng/ml. An optimum concentration is in the range of 10–30 ng/ml, with 20 ng/ml being most preferred. When a member of the FGF family is used, heparan sulphate, a glycosaminoglycan molecule which facilitates the binding of FGF to its receptors can be added to the culture medium at a concentration of 0.2 µg/ml–20 µg/ml, preferably at a concentration of 0.4 µg/ml–4 µg/ml. Most preferred is a concentration of about 2 µg/ml. In a preferred embodiment, the culture medium comprises FGF in combination with a member of the transforming growth factor beta (TGFβ) family. The TGFβ family includes basic myelin proteins (BMP-2, BMP-4, BMP-5, BMP-6, BMP-7), activins A & B, decapentaplegic (dpp), 60A, OP-2, dorsalin, GDFs (1, 3, and 9), nodal, MIS, Inhibin α, transforming growth factors betas (TGF-β1, TGF-β2, TGF-β3, TGF-β5), and glial-derived neurotrophic factor (GDNF) (see Atrisano et al. (1994) *J. Biochemica et Biophysica Acta* vol. 1222: 71–80).

If the TH+ cells are to be used for transplantation purposes or certain drug testing procedures, it is preferable to use a completely defined culture medium that has the nutrients and hormones necessary for supporting the survival of the cells. By "completely defined", it is meant that all of the components of the medium are known. Numerous defined culture media are commercially available. A preferred medium, referred to herein as "Complete Medium", comprises a 1:1 mixture of Dulbecco's Modified Eagle's Medium and F12 nutrient (GIBCO) plus 0.6% glucose, 2 mM glutamine, 3 mM sodium bicarbonate, 5 mM HEPES buffer and a defined hormone mix and salt mixture (Sigma; 10% by volume) that includes 25 $\mu$g/ml insulin, 100 $\mu$g/ml transferrin, 20 $\mu$M progesterone, 50 $\mu$M putrescine, and 30 nM selenium chloride.

The culture medium may comprise conditioned media (CM), which is a culture medium that has been exposed to living cells and thus contains substances, such as growth factors, that have been released by the cells. However, the addition of CM renders the culture medium undefined, and thus is not preferred when the cells are to be used for transplantation purposes and certain drug testing procedures. CM can be obtained from any tissue that can be cultured that will induce dopamine expression in cells derived from normally non-dopaminergic neural tissue and/or will attenuate the effects of a dopamine-inducing growth factor. Any amount of CM can be used (0–100%). Generally, the culture medium will comprise from about 25 to 100% CM. Preferred CMs are derived from glial cells. Particularly preferred are CMs derived from the rat B49 glial cell line [Schubert et al., *Nature,* 249: 224, (1974)] and CM derived from astrocytes.

Primary cell cultures are plated, preferably at a density in the range of about $10^2$ to $10^7$ cells/ml, more preferably at a density of about $10^6$ cells/ml. The cells can then be grown in any suitable container, such as a tissue culture flask, well, or petri dish. The container may or may not have a surface onto which cells can adhere. In cases where it is desirable that cells adhere, it is generally necessary to treat them with a substance that provides an ionically charged surface such as poly-D-lysine, poly-L-ornithine, Matrigel, laminin, fibronectin, and other surfaces known to induce cell attachment. The cells are capable of adhering to certain plastics. However, when glass substrates are used, it may be desirable to treat their surfaces. When adherence is not desired, glass substrates or some untreated plastic tissue culture substrates can be used. A poly-L-ornithine treated culture container provides a particularly suitable surface onto which the cells can adhere. Alternatively, the cells can be co-cultured on a feeder layer bed of any type or combination of types of cells as opposed to on a treated substrate. Preferred for co-culturing is a feeder bed of other neural cells such as neurons, astrocytes or oligodendrocytes derived from any region of the CNS.

The cultures are maintained as close to physiological conditions as possible. The pH should be between pH 6 to 8. Preferably between about pH 7.2 to 7.6, most preferably at a pH of about 7.4. Cells should be kept at a temperature close to physiological levels, between 30 to 40° C., more preferably between about 32 to 38° C. and most preferably between about 35 to 37.5° C. The cells should be maintained in about 5% $CO_2$, 95% $O_2$, and 100% humidity. However, culture conditions may be varied. For example, the addition of 1% fetal bovine serum (FBS) results in an increase in the number of TH+ neurons detected after cultures have been co-cultured on a glial cell feeder layer for 24 hours and also increases the numbers of TH+ cells detected when cells are grown in undefined culture medium in the absence of the feeder layer. One preferred embodiment is to grow primary cells in a culture medium containing CM derived from the rat B49 glial cell line and FGF-2 or a combination of EGF and FGF-2. A preferred embodiment for cells cultured in a defined medium for transplantation and other purposes is to grow primary tissue directly on a substrate-coated surface, such as poly-L-ornithine-coated coverslips, in a defined culture medium (e.g. Complete Medium) and a combination of FGF-2 with activin or BMP-2.

The induction of dopaminergic cells is determined using any method capable of measuring the presence of dopamine, such as immunocytochemistry using antibodies directed against dopamine, or measuring the biochemical activity of dopaminergic cells by measuring dopamine uptake. The presence of precursor molecules involved in the synthesis of dopamine can be measured. For example, immunocytochemical analysis to detect the presence of tyrosine hydroxylase, or assays, such as polymerase chain reaction and in situ hybridization techniques which detect mRNA for enzymes involved in dopamine synthesis are useful tools for measuring the presence of dopaminergic cells. The identification of dopaminergic neurons is accomplished using morphological analysis of neurons or by dual or triple labeling to show the presence of dopamine or dopamine precursors plus immunoreactivity for neuron specific enolase (NSE), the neurofilament proteins tau-1 and MAP-2 or for neu-N (a neuronal nuclear antigen) or $\beta$-tubulin and/or bromodeoxyuridine (BrdU), which labels actively dividing cells.

In Vitro Induction of Dopaminergic Cells Derived from Multipotent Neural Stem Progeny Proliferated In Vitro From Embryonic and Adult Mammalian Neural Tissue Multipotent neural stem cells have been reported and their potential use described [Reynolds and Weiss, *Science,* 255: 1707 (1992); Reynolds et al., *J. Neurosci.,* 12: 4565 (1992); Reynolds and Weiss, *Restorative Neurology and Neuroscience,* 4: 208 (1992); Reynolds and Weiss, *Neuronal Cell Death and Repair,* ed. Cuello (1993)]. Additionally, the utility of these cells is described in published PCT applications no. WO 93/01275, WO 94/16718, WO 94/10292, and WO 94/09119. As used herein, the term "neural stem cell" refers to an undifferentiated multipotent neural stem cell that can be induced to proliferate in vitro in the presence of a proliferation-inducing growth factor such as, amphiregulin, acidic fibroblast growth factor (aFGF or FGF-1), basic fibroblast growth factor (bFGF or FGF-2), transforming growth factor alpha (TGF$\alpha$), and the like. The neural stem cell is capable of self-maintenance, meaning that with each cell division, one daughter cell will also be a stem cell. The non-stem cell progeny (i.e. progenitor cells) of a single multipotent neural stem cell are capable of differentiating into neurons, astrocytes (type I and type II) and oligodendrocytes. Hence, the neural stem cell is "multipotent" because its progeny have multiple differentiative pathways.

The term "neural progenitor cell", as used herein, refers to an undifferentiated cell derived from a neural stem cell, that is not itself a stem cell. A distinguishing feature of a progenitor cell is that, unlike a stem cell, it has limited proliferative ability and thus does not exhibit self-maintenance. It is committed to a particular path of differentiation and will, under appropriate conditions, eventually differentiate into glia or neurons.

The term "precursor cells", as used herein, refers to the progeny of neural stem cells, and thus includes both progenitor cells and daughter neural stem cells.

CNS precursor cells derived from stem cells can be cultured using the methods described in Example 3 below, and in the published PCT applications referenced above. In the embryo, neural stem cell-containing tissue can be obtained from any CNS region, including the striatum, cortex, septum, thalamus, ventral mesencephalon and spinal cord. However, in adult, the neural tissue is preferably obtained from tissue lining the various ventricles and passageways within the CNS. For example, tissue can be obtained from the regions immediately surrounding the lateral (first and second) ventricles and third ventricle of the forebrain, the cerebral aqueduct, the fourth ventricle, and the central canal. Growth factor-responsive stem cells from the neural tissue are grown in a culture medium in the presence of at least one growth factor. The medium is preferably a defined serum-free medium. Growth factors which may be used for inducing proliferation, singly or in combination with other growth factors, include any growth factor which allows precursor cells to proliferate, including any molecule which binds to a receptor on the surface of the cell to exert a trophic, or growth-inducing effect on the cell. Such factors include acidic and basic fibroblast growth factors (FGF-1, and FGF-2), epidermal growth factor (EGF), an EGF-like ligand, amphiregulin, transforming growth factor alpha (TGFα), and the like. The cell is induced to divide giving rise to a cluster of undifferentiated cells that are not immunoreactive for the astrocyte marker, glial fibrillary acidic protein (GFAP); the neuronal markers, neurofilament (NF), microtubule associated protein (MAP-2), and neuron-specific enolase (NSE); or the oligodendrocyte markers, myelin basic protein (MBP) and galactocerebroside (GalC). However, precursor cells within the cluster are immunoreactive for nestin, an intermediate filament protein found in undifferentiated CNS cells. The nestin marker was characterized by Lehndahl et al. [*Cell*, 60: 585–595 (1990)]. The mature phenotypes associated with the neural cell types which may be differentiated from the progeny of the precursor cells are predominantly negative for the nestin phenotype.

In the continued presence of a mitogen such as EGF, FGF or the like, precursor cells within the neurosphere continue to divide resulting in an increase in the size of the neurosphere and the number of undifferentiated cells [nestin(+), GFAP(−), NF(−), MAP-2(−), NSE (−), MBP (−), GalC(−)]. At this stage, the cells are non-adherent and tend to form the free-floating clusters characteristic of neurospheres. However, culture conditions may be varied so that while the precursor cells still express the nestin phenotype, they do not form the characteristic neurospheres.

Differentiation of the cells can be induced by any method known in the art which activates the cascade of biological events which lead to growth, which include the liberation of inositol triphosphate and intracellular $Ca^{2+}$, liberation of diacyl glycerol and the activation of protein kinase C and other cellular kinases, and the like. Treatment with phorbol esters, differentiation-inducing growth factors and other chemical signals can induce differentiation. Differentiation can also be induced by plating the cells on a fixed substrate such as flasks, plates, or coverslips coated with an ionically charged surface such as poly-L-lysine and poly-L-ornithine and the like.

Other substrates may be used to induce differentiation such as collagen, fibronectin, laminin, matrigel, and the like. Differentiation can also be induced by leaving the cells in suspension in the presence of a proliferation-inducing growth factor, without reinitiation of proliferation (i.e. without dissociating the neurospheres).

A preferred method for inducing differentiation of the neural stem cell progeny comprises culturing the cells on a fixed substrate in a culture medium that is free of the proliferation-inducing growth factor. After removal of the proliferation-inducing growth factor, the cells adhere to the substrate (e.g. poly-ornithine-treated plastic or glass), flatten, and begin to differentiate into neurons and glial cells. At this stage the culture medium may contain serum such as 0.5–1.0% fetal bovine serum (FBS). However, for certain uses, if defined conditions are required, serum would not be used. Within 2–3 days, most or all of the neural stem cell progeny begin to lose immunoreactivity for nestin and begin to express antigens specific for neurons, astrocytes or oligodendrocytes as indicated by immunoreactivity for MAP-2, GFAP and GalC, respectively, using immunocytochemistry techniques well known in the art.

In summary, CNS stem cells have been isolated from a variety of embryonic and adult CNS regions including the striatum, the spinal cord, brain stem, and hypothalamus. In each of these cases the isolated CNS stem cell exhibits self-maintenance and ultimately generates a large number of differentiated progeny which include neurons, astrocytes and oligodendrocytes. Thus, stem cells are present in multiple regions of the adult mammalian CNS and can be cultured, in vitro to obtain large numbers of undifferentiated neural cells, whose differentiation may be regulated by the application of growth factors and/or other biological factors. The undifferentiated cells (either as a cell suspension or intact neurospheres) proliferated using these techniques can be cultured to generate dopaminergic cells using the same methods described above for the induction of dopaminergic neurons in primary neural tissue.

Transplantation of Cultured Dopaminergic Cells

Purified populations of differentiated dopaminergic cells, derived from primary culture or from the proliferated precursor progeny of neural stem cells, may be implanted into dopamine deficient regions of the brain of a recipient. Alternatively, cells that have been cultured in a culture medium that induces the formation of dopaminergic cells may be implanted into the brain prior to the completion of the differentiation process. Following implantation, the differentiation of dopaminergic cells may be completed in vivo. Any suitable method for purifying the cells may be used, or the cells could be implanted together with other neural cells. Any suitable method for the implantation of dopaminergic cells or precursor cells near the region of dopamine depletion may be used. Methods taught in U.S. Pat. No. 5,082,670 to Gage et al. for the injection of cell suspensions, such as fibroblasts, into the CNS may be employed for the injection of the differentiated dopaminergic cells prepared by the culture methods disclosed herein. Additional approaches and methods may be found in *Neural Grafting in the Mammalian CNS*, Bjorklund and Stenevi, eds., (1987). Xeno and/or allografts may require the application of immunosuppressive techniques or induction of host tolerance to enhance the survival of the implanted cells.

In some instances, it may be possible to prepare differentiating or differentiated dopaminergic cells from a recipient's own nervous system (for example, from tissue removed during biopsies). In such instances, the dopaminergic cells may be generated in culture from the progeny of neural stem cells. The cells from the dissociated nervous tissue are grown in the presence of a proliferation-inducing growth factor such as EGF or FGF. Upon suitable expansion of numbers, the precursor cells are contacted with a growth factor or a combination of growth factors and/or a conditioned medium or combinations of conditioned media, which induce the differentiation of dopaminergic cells. Preferably, the cells are proliferated and dopamine expression is induced using a defined culture medium. The differentiating or differentiated dopaminergic cells may be implanted into the appropriate region(s) of the recipient's brain.

Drug Screening Using Cultured Dopaminergic Cells

The dopaminergic cells produced using the methods disclosed herein may also be used to screen the effects of drugs and other compounds on dopaminergic cells. The screening methods disclosed in co-pending applications U.S. Ser. No. 08/311,099 now abandoned and U.S. Ser. No. 08/339,090 now abandoned may be used. Generally, the effect of the drugs and other compounds on the ability of the differentiating or differentiated cells to produce and/or metabolize dopamine would be measured.

EXAMPLE 1

Propagation of Primary Cultures

The brains of E14 embryonic albino mice were placed in phosphate buffered saline (PBS) and dissected to obtain the striata, cerebral cortex and mesencephalon. The neural tissue was mechanically dissociated in serum-free medium (Dulbecco's Modified Eagle's Medium (DMEM) and F12 nutrient (GIBCO), using a fire polished Pasteur pipette. Cells were plated at a density of $10^6$ cells/ml on poly-L-ornithine-coated (15 μg/ml; Sigma) glass coverslips in 24 well Nunclon culture dishes in a volume of 0.5 ml/well of Complete Medium or co-cultured on a glial feeder bed. Growth factors and/or conditioned media and/or 1% serum were added to the wells as outlined in Example 6. Cells were incubated at 37° C. in a 95% air/5% $CO_2$ humidified atmosphere.

EXAMPLE 2

Figure 1A:
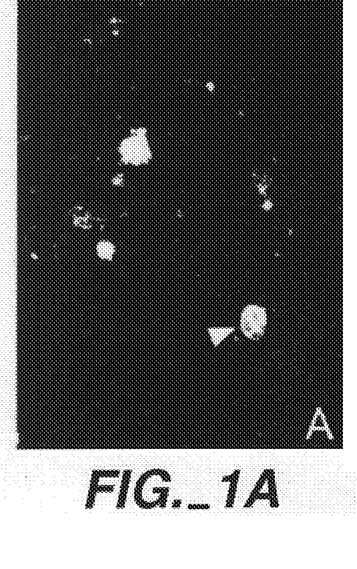
Figure 1B:
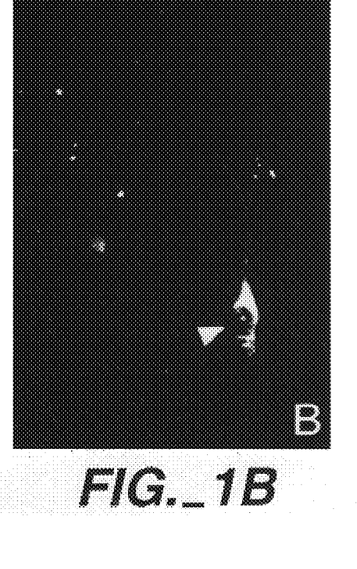

Induction of Tyrosine Hydroxylase Expression in Cells Derived from the Adult Subventricular Zone To label proliferating cells in the subependyma of the subventricular region of the brain, adult $CD_1$ mice were given five injections of BrdU (Sigma, 120 mg/kg) in sterile saline solution, administered at two hour intervals [Morshead and van der Kooy, *J. Neurosci.*, 1: 49 (1992)]. Thirty minutes after the last BrdU injection, the animals were sacrificed. The striata were removed, cut into 1 mm coronal sections and placed in artificial cerebrospinal fluid (aCSF; 124 mM NaCl, 5 mM KCl, 1.3 mM $MgCl_2$, 2 mM $CaCl_2$, 26 mM $NaHCO_3$ and 10 mM D-glucose (pH 7.35, ~280 mOsmol), aerated with 95% $CO_2$ at room temperature. After 15 minutes in the aCSF, the subventricular zones were micro dissected out, cut into small pieces and transferred to a spinner flask (Bellco Glass) with a magnetic stirrer, containing a low-$Ca_2$-aCSF solution (124 mM NaCl, 5 mM KCl, 3.2 mM $MgCl_2$, 0.1 mM $CaCl_2$, 26 mM $NaHCO_3$ and 10 MM D-glucose (pH 7.35, ~280 mOsmol), 1.33 mg/ml of trypsin (9000 BAEF (benzoyl-L-arginine ethylester) units/mg), 0.67 mg/ml of hyaluronidase (2000 units/mg) and 0.2 mg/ml of kynurenic acid. This solution was aerated with 95% $CO_2$/5% $O_2$ at 32° C. to 35° C. After 90 minutes, tissue sections were transferred to normal aCSF for 5 minutes and then placed in DMEM/F12 medium containing 0.7 mg/ml ovomucoid (Sigma). The tissue was mechanically triturated with a fire-narrowed Pasteur pipette. Cells were centrifuged at 400 r.p.m. for 5 minutes and resuspended in Complete Medium with or without conditioned medium (cm) from the rat B49 glial cell line (see example 5) and FGF-2 (20 ng/ml). They were plated onto poly-L-ornithine-coated glass coverslips in 24-well Nunclon tissue culture dishes and incubated at 37° C., 100% humidity, aerated with 95% $CO_2$/5% $O_2$, for three days. The cells were then fixed and processed for dual-label indirect immunocytochemistry for TH and BrdU, as outlined in Example 10. The presence of BrdU labeled cells, which were also TH-IR, only in those cells treated with CM and FGF-2 (FIG. 1), suggest that adult proliferating subventricular zone cells can be induced to express TH in the presence of the CM and growth factor.

EXAMPLE 3

Isolation and Propagation of Embryonic Stem Cells

Embryonic day 14 (E14) $CD_1$ albino mice (Charles River) were decapitated and the brain and striata removed using sterile procedure. The tissue was mechanically dissociated with a fire-polished Pasteur pipette into Complete Medium. The cells were centrifuged at 800 r.p.m. for 5 minutes, the supernatant aspirated, and the cells resuspended in DMEM/F-12 medium for counting. The cells were resuspended in Complete Medium with 16–20 ng/ml EGF (purified from mouse submaxillary, Collaborative Research) or TGFα (human recombinant, Gibco), plated at $0.2 \times 10^6$ cells/ml into 75 $cm^2$ tissue culture flasks (Corning) with no substrate pre-treatment and housed in an incubator at 37° C., 100% humidity, 95% air/5% $CO_2$. The cells proliferated within the first 48 hours and by 3–4 days in vitro (DIV), they formed neurospheres that lifted off the substrate between 4–6 DIV.

After 7 DIV, the neurospheres were removed, centrifuged at 400 r.p.m. for 2–5 minutes, and the pellet was mechanically dissociated into individual cells with a fire-polished glass Pasteur pipet in 2 mls of Complete Medium. $1 \times 10^6$ cells were replated into a 75 $cm^2$ tissue culture flask with 20 mls of the EGF-containing Complete Medium. The proliferation of the stem cells and formation of new neurospheres was reinitiated. This procedure can be repeated every 6–8 days.

EXAMPLE 4

Preparation of Glial Feeder Layers

An astrocyte glial cell feeder layer was prepared from striatal tissue obtained from postnatal mice (0–24 hours). The neural tissue was dissected out, minced and transferred to a 15 ml centrifuge tube containing DMEM/F12 (1:1)/10% FBS. The tissue was dissociated by trituration with a fire polished glass pipette and plated in Coming culture flasks containing 20 ml of DMEM/F12/10% FBS at a density of 150,000 cells/ml. When the primary astrocyte glial cells reached confluency, the cells were dissociated (using trypsin-EDTA) and replated at 200,000 cells/$cm^2$ onto poly-L-ornithine-coated glass coverslips in 24 well culture dishes. After 3 to 4 days, confluency was reestablished. Cells obtained from the culture of primary tissue (Example 1) or 6 day old, BrdU-labelled second passage neurospheres (Example 3) were washed twice and resuspended in fresh medium (free of serum, EGF or BrdU) prior to co-culturing the cells or neurospheres on the astrocyte feeder beds (Examples 6 and 7).

EXAMPLE 5

Preparation of Conditioned Medium

Conditioned medium (CM) was prepared from astrocytic cells or from a rat B49 glial cell line [Schubert et al., *Nature*, 249: 224, (1974)]. An astrocyte glial cell feeder layer was prepared (Example 4). The astrocytic layer was passaged once before collection of the CM. Rat B49 glial cell line cells were cultured under the same conditions as the astrocytic cells. Confluent astrocyte or rat B49 glial cell line cultures were rinsed once with PBS and twice with serum-free Complete Medium and incubated in 20 ml of the same medium. The CM was collected 24, 48 and 72 hours after incubation commenced and centrifuged at 1,000 to 2,000 r.p.m. to remove any cell or debris. The CM was stored at −80° C.

EXAMPLE 6

In vitro Induction of TH-IR in Cells Derived from Primary Culture

Paradigm 1

Primary cultures derived from tissue of the striatum and cerebral cortex were prepared as outlined in Example 1. Complete Medium (control), EGF (20 ng/ml; Chiron), recombinant FGF-2 (20 ng/ml; R&D Systems), a combination of EGF plus FGF, astrocyte (ACM) or rat B49 glial cell line conditioned medium (BCM; see Example 3) were added singly or in combinations to individual wells at the time of plating (time, t=0). 1% FBS (Upstate Biotechnology Incorporated) was added to 50% of the wells which did not receive conditioned medium. Immunocytochemical analysis for the detection of TH+ cells (Example 5) was undertaken 24 hours after plating. Results are summarized in Table 1. The addition of 1% FBS to the CM-free wells caused a three-fold increase in the numbers of TH+ cells recorded in the presence of the growth factors. The combination of FGF-2 plus BCM produced the most profound results, resulting in the generation of, on average, more than approximately 5,000 TH+ cells/cm$^2$.

TABLE I

Average Number Of TH+ Cells Generated Per cm$^2$
From Striatal And Cortical Primary Cultures

|  | STRIATUM |  | CORTEX |  |
| --- | --- | --- | --- | --- |
|  | FBS-free | 1% FBS | PBS-free | 1% FBS |
| control | 4 | 2 | 12 | 29 |
| EGF | 10* | 18 | 14* | 25* |
| FGF | 326 | 1128 | 72 | 295 |
| EGF + FGF | 350 | 1668 | 75 | 229 |
| ACM | 10* | — | — | — |
| ACM + EGF | 10* | — | — | — |
| ACM + FGF | 1468 | — | — | — |
| ACM + E + F | 1645 | — | — | — |
| BCM | 16 | — | — | — |
| BCM + EGF | 26 | — | — | — |
| BCM + FGF | 5397 | — | — | — |
| BCM + E + F | 4470 | — | — | — |

*Increase over control values not significant.
n = 4

Paradigm 2

Cells obtained from primary culture (Example 1) were washed twice and resuspended in fresh medium prior to co-culturing the cells on astrocyte feeder layers (Example 4) in the presence of Complete Medium (control) or Complete Medium plus EGF, FGF-2 or a combination of EGF and FGF-2 (20 ng/ml of each growth factor), 1 μM BrdU and 1% FBS. Indirect immunocytochemistry (Example 10) was carried out on cells that had been cultured for 24 hours. A significant increase in TH-IR was detected in striatal cells co-cultured in the presence of FGF-2 or EGF plus FGF-2 when compared with cells cultured only in Complete Medium. A small, but significant increase was observed in the presence of EGP alone. Primary cells derived from the cortex showed a similar response to EGF and FGF alone (a significant increase over control values) but the largest increase in TH-IR was seen using EGF and FGF-2 together. As indicated by BrdU uptake, few cells from the mesencephalon are mitotically active, even in the presence of growth factors. The results are summarized in Table II.

TABLE II

| Source of Primary | CONTROL Number of Cells/cm$^2$ | | EGF Number of Cells/cm$^2$ | | FGF Number of Cells/cm$^2$ | | EGF + FGF Number of Cells/cm$^2$ | |
| --- | --- | --- | --- | --- | --- | --- | --- | --- |
| Tissue | TH+ | TH + BrdU+ | TH+ | TH + BrdU+ | TH+ | TH + BrdU+ | TH+ | TH + BrdU+ |
| Cortex | 50 | 1 | 143 | 3 | 148 | 25 | 216 | 46 |
| Striatum | 94 | 19 | 139 | 60 | 1475 | 460 | 1311 | 498 |
| Mesencephalon | 472 | 2 | 759 | 3 | 512 | 4 | 409 | 3 |

EXAMPLE 7

In Vitro Induction of TH expression using a Defined Culture Medium

Primary cultures derived from tissue of the striatum and cerebral cortex were prepared as outlined in Example 1. Complete Medium (control), FGF-2 (20 ng/ml; R&D systems), BMP-2 (50 ng/ml; Chiron Corp.) and activin (50 ng/ml; Chiron Corp.) were added singly or in combination (Complete Medium plus FGF-2 and BMP-2 or Complete Medium plus FGF-2 and activin) to individual wells at the time of plating. Immunocytochemical analysis for the detection of TH+ cells (Example 10) was undertaken 24 hours after plating. Results are summarized in Table 3. The combination of FGF-2 plus activin or FGF-2 plus BMP-2 produced the most profound results, resulting in the generation of, on average, approximately 5,000 TH+ neurons per cm$^2$. In contrast, the control, comprising Complete Medium alone, produced an average of 2 TH+ cells per cm$^2$.

TABLE 3

Number of TH+ immunoreactive cells per cm$^2$

| MEDIUM SUPPLEMENT | #TH+ CELLS |
| --- | --- |
| No supplement (control) | 2 ± 1 |
| FGF-2 | 210 ± 29 |
| BMP-2 | 2 ± 1 |
| Activin | 0 |
| FGF-2 + BMP-2 | 4622 ± 1207 |
| FGF-2 + Activin | 4930 ± 289 |

EXAMPLE 8

In Vitro Induction of TH-IR in Neural Stem Cell-Derived Precursor Cell Progeny Using Conditioned Medium Paradigm 1

Figure 2A:
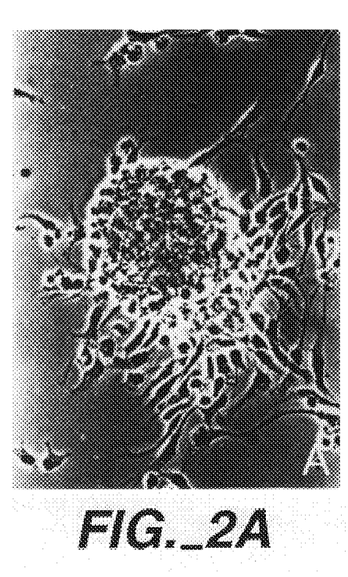
Figure 2B:
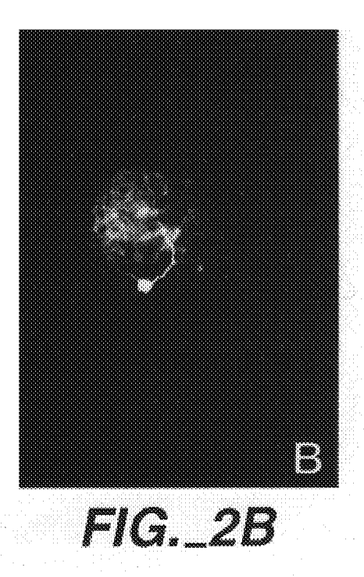
Figure 3A:
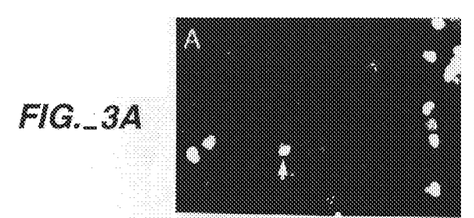
Figure 3B:
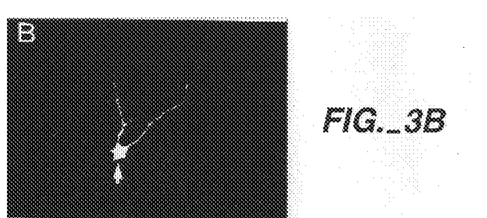
Figure 3C:
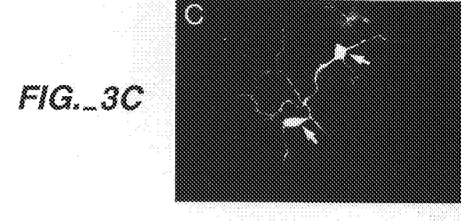
Figure 3D:
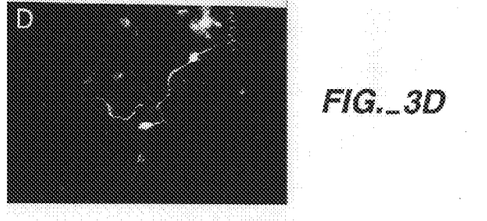

Single, undissociated 6 day old primary generated neurospheres (see Example 3) were plated onto poly-L-ornithine coated glass coverslips, in Complete Medium with or without rat B49 glial cell line-derived CM (Example 5)+20 ng/ml FGF-2, and incubated at 37° C. in 5% $CO_2$, 95% air, 100% humidity. 24 hours after plating, indirect immunocytochemistry for TH+ (see Example 10) revealed the presence of TH+ cells, with processes and a neuronal morphology, in the wells containing CM and FGF-2 (FIG. 2) but not in the wells containing only Complete Medium.

Paradigm 2

Single, undissociated six day old, second passage neurospheres (Example 3) were labeled with BrdU, washed twice and resuspended in fresh medium prior to co-culturing the neurospheres on astrocyte feeder layers (Example 4) in the presence of Complete Medium or Complete Medium plus FGF-2 (20 ng/ml). Indirect immunocytochemistry (Example 10) was carried out on cells that had been cultured for 24 hours. TH-IR cells with neuronal morphology that stained positive for MAP-2 were observed in the neurospheres cultured with FGF-2. Several of the TH+ cells showed BrdU immunoreactivity (FIG. 3).

EXAMPLE 9

In Vitro Induction of TH-IR in Neural Stem Cell-Derived Progeny Using Defined Medium Single, undissociated 6 day old primary generated neurospheres (see Example 3) are plated onto poly-L-ornithine coated glass coverslips, in Complete Medium with a combination of 20 ng/ml FGF-2 and 20 ng/ml BMP-2 or a combination of 20 ng/ml FGF-2 and 20 ng/ml activin (Example 7), and incubated at 37° C. in 5% $CO_2$, 95% air, 100% humidity. The number of dopaminergic neurons is determined by TH-immunoreactivity (Example 11).

EXAMPLE 10

Immunocytochemistry

Cells were fixed with 4% paraformaldehyde for 30 minutes followed by three washes in PBS for 10 minutes each. The cells were incubated with a primary anti TH antibody (rabbit polyclonal, 1:1,000, Engene Tech International Inc.; or 1:100, Pel-freeze) prepared in PBS/10% normal goat serum/0.3 Triton X-100 for 2 hours at 37° C. Following three rinses in PBS, goat anti-rabbit rhodamine (Jackson) was applied in PBS for 30 minutes at room temperature. In some cases, MAP-2 (Boehringer-Mannheim) was used to identify neurons. Cells were then washed three times for 10 minutes each in PBS, rinsed with water, placed on glass slides and coverslipped using FLUOROSAVE (Calbiochem) as the counting medium. The number of dopaminergic neurons was determined by counting all the TH-immunoreactive (TH+) per $cm_2$, under 200× magnification.

EXAMPLE 11

Transplantation of Dopaminergic Cells

Parkinson's disease is a condition characterized by degeneration of the dopaminergic pathway to the striatum and results from decreased dopamine levels in this region. The condition is characterized by muscular rigidity, tremor, and other motor abnormalities. Precursor cells, prepared from fetal tissue by the method of Example 3 are proliferated and induced to differentiate into dopaminergic cells (Example 7 or 8). Dopaminergic cells are stereotactically injected into the striatum of a Parkinsonian patient. Booster injections may be performed if required. Alternatively, precursor cells are prepared from neural tissue obtained from a biopsy of the Parkinsonian patient's and induced to differentiate into dopaminergic cells (Example 7 or 8) and stereotactically injected into the striatum of the patient. Alternatively, the precursor cells can be cultured in the presence of a culture medium that induces the formation of dopaminergic cells and implanted into the striatum of a Parkinsonian patient where the precursor cells differentiate, in vivo, into dopaminergic cells. Improved motor control is used to measure the success of the transplantation.

EXAMPLE 12

Drug Screening Using Cultured Dopaminergic Cells

PROZAC, a drug widely used in the treatment of psychiatric illness, is added to cultured dopaminergic cells prepared as outlined in Examples 6 or 7 in concentrations ranging from 1 ng/ml to 1000 ng/ml. The effects of the drug at various concentrations with respect to cell metabolism and survival is monitored.

All references, patents, and patent applications cited herein are incorporated herein by reference.

What is claimed is:

1. A method for inducing the expression of tyrosine hydroxylase in neural cells in vitro comprising culturing mammalian CNS neural cells derived from normally non-dopaminergic, non-tumorigenic tissue in a culture medium to which has been added at least one member of the fibroblast growth factor family and at least one member of the transforming growth factor beta family wherein tyrosine hydroxylase is expressed.

2. The method of claim 1 wherein said culture medium is defined, said member of the fibroblast growth factory family is FGF-2 and said culture medium comprises a member of the transforming growth factor beta family selected from the group consisting of activin and bone morphogenic protein-2.

3. The method of claim 1 wherein said normally non-dopaminergic tissue is neural tissue selected from the group consisting of the striatum and the cortex.

4. The method of claim 1 wherein said culture medium further comprises serum.

5. The method of claim 1 wherein said neural cells are cultured in the absence of a feeder layer.

6. The method of claim 1 wherein said neural cells are primary cells obtained from embryonic tissue.

7. The method of claim 1 wherein said culture medium is defined.

8. The method of claim 1 wherein said neural cells are cultured on an ionically charged surface selected from the group consisting of poly-D-lysine, poly-L-ornithine, MATRIGEL™, laminin, and fibronectin.

9. The method of claim 8 wherein said charged surface is poly-L-ornithine.

10. The method of claim 1 wherein said neural cells are the progeny of at least one multipotent neural stem cell which was induced to proliferate in vitro by the presence of one or more growth factors.

11. The method of claim 10 wherein said multipotent neural stem cell is derived from juvenile or adult neural tissue.

12. The method of claim 1 wherein said neural cells are primary cells.

13. The method of claim 12 wherein said member of the fibroblast growth factor family is FGF-2 and said member of the transforming growth factor beta family is selected from the group consisting of activin and bone morphogenic protein-2.

14. A method of providing dopaminergic cells to a patient comprising transplanting neural cells which are mammalian CNS neural cells derived from normally non-dopaminergic, non-tumorigenic tissue in a culture medium to which has been added at least one member of the fibroblast growth factor family and at least one member of the transforming growth factor beta family to induce the expression of tyrosine hydroxylase in said neural cells into said patient's CNS.

15. The method of claim 14 wherein said patient has Parkinson's disease and said neural cells are administered to said patient's striatum.

16. The method of claim 14 wherein said member of the fibroblast growth factor family is FGF-2 and said member of the transforming growth factor beta family is selected from the group consisting of activin and bone morphogenic protein.

17. The method of claim 14 wherein said culture medium is defined.

18. The method of claim 14 wherein said neural cells are obtained from the CNS of said patient.

19. A method of screening the effects of a drug on dopaminergic cells comprising culturing mammalian CNS neural cells derived from normally non-dopaminergic, non-tumorigenic tissue in a culture medium to which has been added at least one member of the fibroblast growth factor family and at least one member of the transforming growth factor beta family to induce the expression of tyrosine hydroxylase in said neural cells contacting said neural cells with a drug and measuring the response, selected from the group consisting of a dopaminergic response and cell survival, of said dopaminergic cells to said drug.

20. The method of claim 19 wherein said effects are determined by measuring the ability of said cells to produce or metabolize dopamine.

21. A cell culture comprising tyrosine-hydroxylase-expressing cells prepared by the method of claim 1.

22. The cell culture of claim 21, wherein said culture medium is defined, said member of the fibroblast growth factor family is FGF-2 and said member of the transforming growth factor beta family is selected from the group consisting of activin and bone morphogenic protein-2.

23. The cell culture of claim 21 which is cultured on an ionically charged surface selected from the group consisting of poly-D-lysine, poly-L-ornithine, MATRIGEL™, laminin, and fibronectin.

24. The cell culture of claim 21 wherein said normally non-dopaminergic CNS tissue is selected from the group consisting of the striatum and the cortex.

25. The cell culture of claim 21 wherein said culture medium further comprises conditioned medium selected from the group consisting of astrocyte conditioned medium and glial cell conditioned medium.

26. The cell culture of claim 21 wherein said neural cells are the progeny of at least one multipotent neural stem cell proliferated in vitro in the presence of one or more growth factors which induced proliferation of said at least one multipotent neural stem cell.

27. The cell culture of claim 26 wherein said multipotent neural stem cell is derived from adult neural tissue.

28. The method of claim 1 wherein said culture medium further comprises at least one member selected from the group consisting of a feeder layer bed of cells and cell conditioned medium.

29. The method of claim 28 wherein said member of the fibroblast growth factor family is FGF-2 and said member of the transforming growth factor beta family is selected from the group consisting of activin and bone morphogenic protein-2.

30. The method of claim 28 wherein said culture medium comprises cell conditioned medium selected from the group consisting of astrocyte conditioned medium and glial cell conditioned medium.

31. The method of claim 30 wherein said cell conditioned medium is derived from rat B49 glial cell line.

32. A method for inducing the expression of tyrosine hydroxylase in neural cells in vitro comprising preparing a cell culture comprising mammalian CNS neural cells derived from normally non-dopaminergic neural tissue and a culture medium to which has been added at least one member of the fibroblast growth factor family and wherein said culture medium additionally comprises a member selected from the group consisting of a feeder layer bed of cells, cell conditioned medium, and members of the TGFβ family to induce the expression of tyrosine hydroxylase in said neural cells.

33. The method of claim 32 wherein said culture medium further comprises serum.

34. The method of claim 32 wherein said neural cells are the progeny of at least one multipotent neural stem cell proliferated in vitro in the presence of one or more growth factors which induced proliferation of said at least one multipotent neural stem cell.

35. The method of claim 32 wherein said normally non-dopaminergic tissue is selected from the group consisting of the striatum and the cortex.

36. The method of claim 32 wherein said culture medium comprises a feeder layer bed derived from normally non-dopaminergic neural tissue.

37. The method of claim 36 wherein said culture medium further comprises serum.

38. The method of claim 32 wherein said culture medium comprises cell conditioned medium.

39. The method of claim 38 wherein said cell conditioned medium is derived from glial cells.

40. The method of claim 38 wherein said cell conditioned medium is derived from astrocytes.

41. The method of claim 38 wherein said cell conditioned medium is derived from rat B49 glial cell line.

* * * * *